US007964701B2

(12) United States Patent
Andersen et al.

(10) Patent No.: US 7,964,701 B2
(45) Date of Patent: Jun. 21, 2011

(54) ALPHA-FETOPROTEIN PEPTIDES

(75) Inventors: Thomas T. Andersen, Albany, NY (US); James A. Bennett, Delmar, NY (US); Herbert Jacobson, Albany, NY (US)

(73) Assignee: Albany Medical College, Albany, NY (US)

( * ) Notice: Subject to any disclaimer, the term of this patent is extended or adjusted under 35 U.S.C. 154(b) by 0 days.

(21) Appl. No.: 12/410,612

(22) Filed: Mar. 25, 2009

(65) Prior Publication Data
US 2009/0203624 A1 Aug. 13, 2009

Related U.S. Application Data

(63) Continuation-in-part of application No. 11/678,784, filed on Feb. 26, 2007, now Pat. No. 7,598,342.

(60) Provisional application No. 60/776,644, filed on Feb. 24, 2006.

(51) Int. Cl.
*A61K 38/00* (2006.01)
*A61K 38/04* (2006.01)
*A61K 38/08* (2006.01)
(52) U.S. Cl. ...... 530/328; 514/10.2; 514/19.4; 514/21.6
(58) Field of Classification Search .......... None
See application file for complete search history.

(56) References Cited

U.S. PATENT DOCUMENTS

| | | | | |
|---|---|---|---|---|
| 5,674,842 | A | 10/1997 | Mizejewski | 514/12 |
| 5,707,963 | A | 1/1998 | Mizejewski | 514/12 |
| 6,121,236 | A * | 9/2000 | Ben-Sasson | 514/12 |
| 6,306,832 | B1 | 10/2001 | Pietras | 514/44 |
| 6,348,567 | B1 | 2/2002 | Krystal et al. | 530/300 |
| 6,818,741 | B2 | 11/2004 | Andersen et al. | 530/328 |
| 7,122,522 | B2 | 10/2006 | Andersen et al. | 514/15 |
| 7,132,400 | B2 | 11/2006 | Andersen et al. | 514/12 |
| 2005/0271587 | A1 | 12/2005 | Andersen et al. | 424/1.69 |

OTHER PUBLICATIONS

Joseph et al., 2009, Journal of Peptide Science, vol. 15, pp. 319-325.*
Jacobson et al , "Inhibition of Estrogen-dependent Breast Cancer Growth by a Reaction Product of α-Fetoprotein and Estradiol", *Cancer Research* vol. 50, 415-420, Jan. 15, 1990.
Bennett et al., "α-Fetoprotein Derived from a Human Hepatoma Prevents Growth of Estrogen-dependent Human Breast Cancer Xenografts", *Clinical Cancer Research*, vol. 4, 287-2884, Nov. 1998.
Mesfin et al., "Development of a synthetic cyclized peptide derived from α-fetoprotein that prevents the growth of human breast cancer", *J. Peptide Res.*, 2001, vol. 58, 246-256.
Defreest et al., "Synthetic peptide derived from α-fetoprotein inhibits growth of human breast cancer: investigation of the pharmacophore and synthesis optimization", *J. Peptide Res.*, 2004, vol. 63, 409-419.
Bennett et al., "A peptide derived from alpha-fetoprotein prevents the growth of estrogen-dependent human breast cancers sensitive and resistant to tamoxifen", *PNAS*, 2002; vol. 99, 2211-2215.
Eisele et al., "Studies on a growth-inhibitory peptide derived from alpha-fetoprotein and some analogs", *J. Peptide Res.*, 2001, vol. 57, 29-38.
Eisele et al., "Studies on analogs of a peptide derived from alpha-fetoprotein having antigrowth properties", *J. Peptide Res.*, 2001, vol. 57, 539-546.
Aggarwal et al., "Synthesis and Screening of a Random Dimeric Peptide Library Using the One-Bead-One Dimer Combinatorial Approach", *Bioconjugate Chem.*, 2006, vol. 17, 335-340.
Aggarwal et al., "A Dimeric Peptide that Binds Selectively to Prostate-Specific Membrane Antigen and Inhibits its Enzymatic Activity", *Cancer Res 2006*, vol. 66: (18): 9171-9177 Sep. 15, 2006.
O'Leary et al., "Design of Potent Peptide Mimetics of Brain-derived Neurotrophic Factor", *The Journal of Biological Chemistry*, vol. 278, No. 28, Jul. 11, 2003, 25738-25744.
Kirschner et al., "Computational Design and Experimental Discovery of an Anti-estrogenic Peptide Derived from Alpha-Fetoprotein", *J. Am. Chem. Soc.*, 2007, vol. 129(19), 6263-6268.
Parikh et al., "Prevention of N-Methyl-N-Nitrosourea-Induced Breast Cancer by α-Fetoprotein (AFP)—Derived Peptide, a Peptide Derived from the Active Site of AFP", *Clin Cancer Res*, 2005; 11(23) Dec. 1, 2005; 8512-8520.
Mizejewski et al., "α-Fetoprotein growth inhibitory peptides: Potential leads for cancer therapeutics", *Mol Cancer Ther.*, 2003;2: 1243-1255.
Mesfin et al., "Alpha-fetoprotein-derived antiestrotrophic octapeptide", *Biochimica et Biophysica Acta* 1501 (2000) 33-43.
Joseph et al., Antiestrogenic and anticancer activities of peptides derived from the active site of alpha-fetoprotein, *Journal of Peptide. Science*, 2008, 14; 1-7.

* cited by examiner

*Primary Examiner* — Robert Landsman
*Assistant Examiner* — Ian Dang
(74) *Attorney, Agent, or Firm* — Heslin Rothenberg Farley & Mesiti P.C.; Kathy Smith Dias

(57) ABSTRACT

The invention relates to compounds that include peptides that inhibit estrogen receptor dependent cell proliferation. The compounds of the invention are useful for treating cell proliferative disorders or physiological conditions characterized by undesirable or unwanted estrogen induced cell proliferation, including breast cancer.

8 Claims, 7 Drawing Sheets

```
                       SEQUENCE LISTING

<160> NUMBER OF SEQ ID NOS: 44

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Met Thr Pro Val Asn Pro Gly
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Pro Val Asn
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline

<400> SEQUENCE: 3

Thr Xaa Val Asn
1

<210> SEQ ID NO 4
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Pro Val Asn Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline

<400> SEQUENCE: 5

Thr Xaa Val Asn Pro
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline

<400> SEQUENCE: 6

Thr Pro Val Asn Xaa
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline

<400> SEQUENCE: 7

Thr Xaa Val Asn Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

```
Pro Val Asn Pro Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline

<400> SEQUENCE: 9

Xaa Val Asn Xaa Gly
1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Val Asn Pro
1

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline

<400> SEQUENCE: 11

Lys Thr Xaa Val Asn
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline

<400> SEQUENCE: 12

Val Asn Xaa Gly
1

<210> SEQ ID NO 13
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline

<400> SEQUENCE: 13

Xaa Val Asn Xaa
1

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Pro Val Asn Pro
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline

<400> SEQUENCE: 15

Ser Xaa Val Asn Pro
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline

<400> SEQUENCE: 16

Ser Pro Val Asn Xaa
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
```

-continued

```
<220> FEATURE:
<221> NAME/KEY: MOD_RES
<222> LOCATION: (5)..(5)
<223> OTHER INFORMATION: Hydroxyproline

<400> SEQUENCE: 17

Ser Xaa Val Asn Xaa
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Pro Val Asn Pro
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline

<400> SEQUENCE: 19

Val Xaa Val Asn Pro
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline

<400> SEQUENCE: 20

Val Pro Val Asn Xaa
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline

<400> SEQUENCE: 21

Val Xaa Val Asn Xaa
```

```
<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Pro Val Asn Pro
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline

<400> SEQUENCE: 23

Ala Xaa Val Asn Pro
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline

<400> SEQUENCE: 24

Ala Pro Val Asn Xaa
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline

<400> SEQUENCE: 25

Ala Xaa Val Asn Xaa
1               5

<210> SEQ ID NO 26
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 26

Thr Ser Val Asn Pro
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline

<400> SEQUENCE: 27

Thr Ser Val Asn Xaa
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Pro Val Asn Thr Pro Val Asn
1               5

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Pro Val Asn Gly Gly Gly Gly Thr Pro Val Asn Gly Gly Gly Gly
1               5                   10                  15

Thr Pro Val Asn
            20

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (15)..(15)
<223> OTHER INFORMATION: Hydroxyproline

<400> SEQUENCE: 30

-continued

Thr Pro Val Asn Xaa Thr Pro Val Asn Xaa Thr Pro Val Asn Xaa
1               5                   10                  15

<210> SEQ ID NO 31
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (23)..(23)
<223> OTHER INFORMATION: Hydroxyproline

<400> SEQUENCE: 31

Thr Pro Val Asn Xaa Gly Gly Gly Gly Thr Pro Val Asn Xaa Gly Gly
1               5                   10                  15

Gly Gly Thr Pro Val Asn Xaa
            20

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (21)..(21)
<223> OTHER INFORMATION: Hydroxyproline

<400> SEQUENCE: 32

Thr Pro Val Asn Xaa Lys Lys Lys Thr Pro Val Asn Xaa Lys Lys Lys
1               5                   10                  15

Thr Pro Val Asn Xaa
            20

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline

<400> SEQUENCE: 33

```
Glu Lys Thr Xaa Val Asn Xaa Gly Asn
1               5
```

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline

<400> SEQUENCE: 34

```
Thr Xaa Val Asn Xaa Gly Asn Glu Lys
1               5
```

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline
<220> FEATURE:
<221> NAME/KEY: MOD_RES
<222> LOCATION: (6)..(6)
<223> OTHER INFORMATION: Hydroxyproline

<400> SEQUENCE: 35

```
Lys Thr Xaa Val Asn Xaa Gly
1               5
```

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline
<220> FEATURE:
<221> NAME/KEY: MOD_RES
<222> LOCATION: (6)..(6)
<223> OTHER INFORMATION: Hydroxyproline

<400> SEQUENCE: 36

```
Lys Thr Xaa Val Asn Xaa
1               5
```

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Met Thr Pro Val Asn Pro Gly
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Thr Pro Val Asn Pro Gly
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline
<220> FEATURE:
<221> NAME/KEY: MOD_RES
<222> LOCATION: (6)..(6)
<223> OTHER INFORMATION: Hydroxyproline

<400> SEQUENCE: 39

Met Thr Xaa Val Asn Xaa Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydroxyproline

<400> SEQUENCE: 40

Glu Met Thr Xaa Val
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydroxyproline

<400> SEQUENCE: 41

Glu Lys Thr Xaa Val
1               5

<210> SEQ ID NO 42
<211> LENGTH: 5
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 42

Glu Lys Thr Pro Val
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Met Thr Pro Val
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Gly Val Gly Gln
1               5
```

US 7,964,701 B2

ALPHA-FETOPROTEIN PEPTIDES

CROSS REFERENCE TO RELATED APPLICATIONS

This application is a continuation-in-part of non-provisional application Ser. No. 11/678,784 filed on Feb. 26, 2007, which issued on Oct. 6, 2009 as U.S. Pat. No. 7,598,342 and which claims priority to U.S. provisional application Ser. No. 60/776,644 filed Feb. 24, 2006, the disclosures of which are hereby incorporated by reference.

GOVERNMENT SUPPORT

The present application was made with support from the National Institutes of Health Grant Nos. 5R01 CA102540 and R15 CA115524 and Department of Defense Grant Nos. W81XWH-04-1-0486 and BC031067; National Science Foundation Grant Nos. CHE-0457275, CHE-0116435 and CHE-0521063. The U.S. Government has certain rights in this invention.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 410018B_Sequence_Listing.txt, a creation date of Jan. 16, 2009, and a size of 11.7 KB. The sequence listing filed via EFS-Web is part of the specification and is hereby incorporated in its entirety by reference herein.

FIELD OF THE INVENTION

The invention relates to peptides derived from alpha-fetoprotein and their use to treat and/or prevent cancer, including breast cancer, glioblastoma, malignant and benign tumors in the ovaries, uterus, prostate, and thyroid.

BACKGROUND OF THE INVENTION

Alpha-fetoprotein (AFP) is an embryo specific serum alpha-globulin glycoprotein that is synthesized in the fetal yolk sac and circulates through the serum of pregnant women (G.I. Abelev 1971). In the last several decades, clinical researchers have investigated the potential anti-estrogen and anti-breast cancer activities of AFP (Jacobson et al. 1990). A number of studies have since shown its effectiveness as a therapeutic agent to treat estrogen-dependent breast cancer, as well as its ability to prevent pre-malignant foci from developing into breast cancer. Specifically, these studies indicate that alpha-fetoprotein (AFP) interferes with estrogen-dependent responses, including the growth-promoting effects of estrogen on breast cancer (Bennett et al. 1998). U.S. Pat. Nos. 5,674,842 and 5,707,963 relate to a 34-amino acid peptide derived from alpha-fetoprotein that was shown to exhibit anti-estrotrophic activity. Subsequently, an 8-amino acid stretch of AFP, EMTPVNPG, (SEQ ID NO. 1), referred to as peptide P472-2, has was identified as possessing anti-estrotrophic activity (Mesfin et al. 2000). Furthermore, U.S. Pat. No. 6,818,741 describes a peptide of eight to twenty amino acids, including a cyclic peptide (9-mer) that is useful in reducing estrogen-stimulated growth of cells.

Previous efforts to identify a peptide under eight residues resulted in the loss of anti-estrotrophic activity (DeFreest et al. 2004.) To date, the specific binding mechanism of AFP and of P472-2 is not known, making rational development of lead compounds difficult.

SUMMARY OF THE INVENTION

The present invention provides small peptides, in some embodiments four to seven amino acids in length that are derived from an active site of alpha-fetoprotein. Surprisingly, the peptides of the present invention retain the anti-estrotrophic activity of the 34-mer (P447) and 8-mer (P472-2) previously identified. It also provides for a unique, previously undisclosed modification of amino acids within the active site of AFP, namely TOVNOGNEK (SEQ ID NO.: 34.

In one aspect, therefore, the present invention relates to a synthetic peptide four to seven amino acids in length, wherein the peptide comprises an amino acid sequence of a) $AA_1$-$AA_2$-$AA_3$-N, wherein $AA_1$ is threonine, serine, valine or alanine; $AA_2$ is proline, hydroxyproline or serine; and $AA_3$ is valine, isoleucine, leucine or threonine;

b) $AA'_1$-$AA'_2$-$AA'_3$-N-$AA'_4$, wherein $AA'_1$ is threonine, serine, valine or alanine; $AA'_2$ is proline, hydroxyproline or serine; $AA'_3$ is valine, isoleucine, leucine or threonine; and $AA'_4$ is proline or hydroxyproline; or c) $AA_1$-$AA_2$-N-$AA_3$, wherein $AA''_1$ is proline, hydroxyproline or serine; $AA''_3$ is valine, isoleucine, leucine or threonine; and $AA''_3$ is proline or hydroxyproline;

and wherein the peptide has anti-estrotrophic activity.

In another aspect, the invention relates to a peptide comprising an amino acid sequence selected from TPVN (SEQ ID NO.: 2), TOVN (SEQ ID NO.: 3), TPVNP (SEQ ID NO.: 4), TOVNP (SEQ ID NO.: 5), TPVNO (SEQ ID NO.: 6), TOVNO (SEQ ID NO.: 7), PVNPG (SEQ ID NO.: 8),OVNOG (SEQ ID NO.: 9), KTOVN (SEQ ID NO.: 11), KTOVNO (SEQ ID NO.: 36), KOTVNOG (SEQ ID NO.: 35), KTPVNPG (SEQ ID NO.: 38) and TOVNOGNEK (SEQ ID NO.: 34).

In yet another aspect, the invention relates to a synthetic linear peptide comprising the amino acid sequence TOVNOGNEK (SEQ ID NO.: 34)

In a related aspect, the invention relates to analogs of the peptides of the invention, polymeric or multimeric forms of the peptides that retain the activity of the unit peptide, as well as pharmaceutical compositions comprising the anti-estrotrophic peptides of the invention. Additionally, peptides comprising one or more tandem repeats of an amino acid sequence disclosed herein, are encompassed by the invention. The tandem repeats may be separated by at least one spacer amino acid.

In another aspect, the invention relates to pharmaceutical compositions comprising a peptide of the invention and a pharmaceutically acceptable carrier. In yet another aspect, the invention relates to a method of inhibiting the estrogen-dependent growth of cells, including breast tumor cells, using an anti-estrotrophic peptide of the invention. Accordingly, the peptide of the invention is useful in the treatment of diseases associated with estrogen-dependent growth, including breast cancer and uterine fibroids. Furthermore, the peptide of the invention may be used in conjunction with other breast cancer therapies, for example, to potentiate the efficacy of tamoxifen.

DETAILED DESCRIPTION OF THE INVENTION

Figure 1:
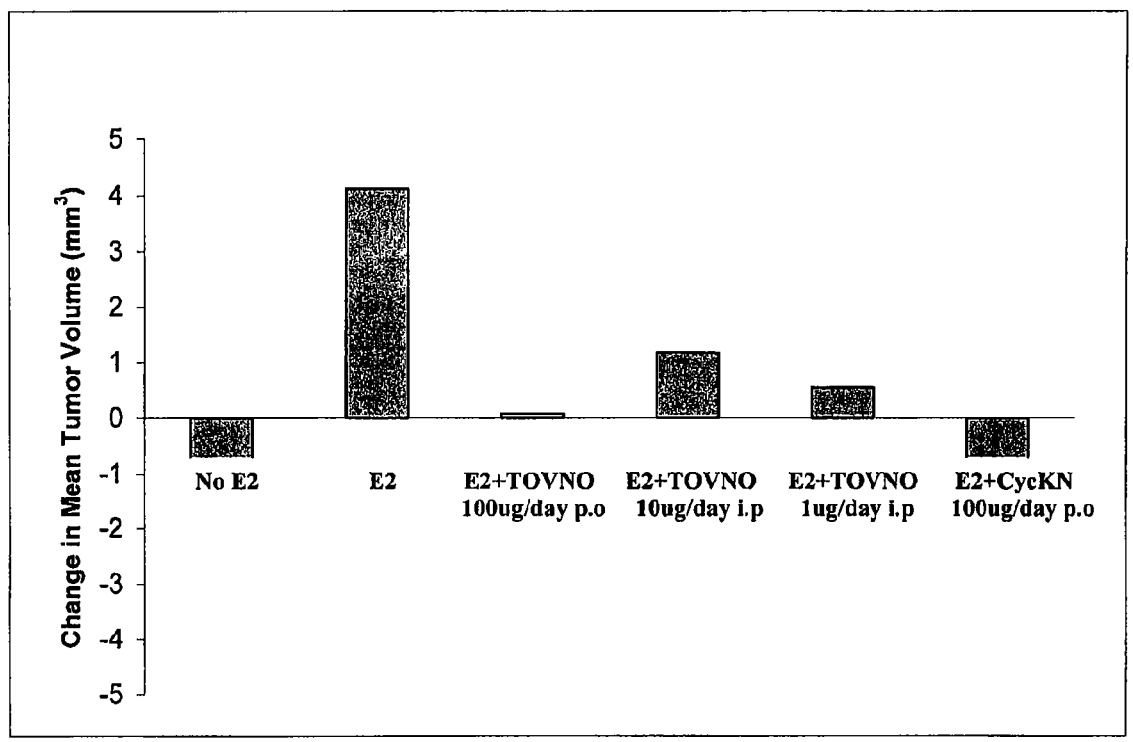
FIG. 1 is a graph showing the effect of a peptide of the invention on estrogen-dependent tumor growth in an MCF7 xenograft model.

All publications, patents and other references cited herein are incorporated by reference in their entirety into the present disclosure.

The invention provides compounds including peptides and peptidomimetics that inhibit estrogen receptor dependent cell proliferation. The compounds of the invention are, therefore, useful for treating cell proliferative disorders or physiological conditions, including breast cancer, characterized by undesirable or unwanted estrogen induced cell proliferation.

In the description that follows, certain conventions will be followed as regards the usage of terminology.

The term "peptide", as that term is know to those of skill in the art, refers to a molecule comprising two or more amino acids, generally fewer than fifty, where the alpha-carboxylic group of one is bound to the alpha-amino group of the other. The universal one letter code known to those skilled in the art is used herein for the identification of the twenty basic amino acids. Additionally, the one letter code, "O" is used herein to designate hydroxyproline, a hydroxylated derivative of proline.

In one embodiment, the present invention encompasses peptides of 4-7 amino acids in length and larger peptides comprising the basic (unit) 4-7-mer, that are polymeric or multimeric forms thereof. In one embodiment, for example, a peptide of the invention might comprise tandem repeats of a unit sequence with (SEQ ID NO.:29) or without (SEQ ID NO.:28) an intervening amino acid.

In another embodiment, the invention encompasses a peptide comprising the amino acid sequence, TOVNOGNEK (SEQ ID NO.: 34) and analogs thereof, including polymeric, multimeric and tandem repeat forms. The invention further encompasses pharmaceutical compositions comprising TOVOGNEK (SEQ ID NO.: 34)and appropriate excipients and stabilizers.

The terms "mimetic", "peptide mimetic" and "peptidomimetic" are used interchangeably, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

The term "anti-estrotrophic activity" refers to the ability of the peptides of the invention to inhibit or reduce the level of estrogen-dependent proliferation in an estrogen receptor-positive ($ER^+$) cell population. Such activity can be measured in a variety of ways, including the immature mouse uterine growth assay as described by Bennett et al. 1998 and the human breast cancer xenograft assay as described by Bennett et al. 1998 and Jacobson et al. 1990.

The term "prevent" as that term is understood by the person of ordinary skill in the medical art (to which the present method claims are directed) is not an absolute term. In the medical art it is understood to refer to the prophylactic administration of a drug to substantially diminish the likelihood or seriousness of a condition. In the present context, the term refers to the ability of the peptides of the invention to lower incidence of palpable tumors, increase latency period and lower tumor multiplicity. The term is not intended to imply absolute protection from disease; rather it applies if there is a diminution in incidence and/or severity.

Peptides of the Invention

In one embodiment, the present invention relates to peptides four to seven amino acids in length comprising an amino acid sequence contained within amino acids 489-496 of human alpha-fetoprotein (Genbank accession no. AAB58754), that is, EMTPVNPG (SEQ ID NO: 1), and analogs thereof.

In another embodiment, the present invention relates to peptides 9 or more amino acids in length comprising the amino acid sequence TOVNOGNEK (SEQ ID NO. 34).

Additionally, multimeric forms of the peptides are also encompassed by the invention. Multimeric forms include dimers, trimers, etc. of one of the peptides of the invention; the synthesis of dimeric peptides, for example, is well known to those of skill in the art (see O'Leary and Hughes, Journal of Biological Chemistry 278(28): 25738-25744, Aggarwal et al., Bioconjugate Chem. 17(2): 335-340, 2006, and Aggarwal et al., Cancer Research, 66: 9171-9177, 2006.) Multimeric forms may be homo- or hetero-multimers, that is they comprise two or more identical peptides or two or more different peptides, respectively.

In another embodiment, the invention provides for larger polymeric peptides that contain tandem repeats of one or more unit peptides with or without one or more spacer amino acids separating the tandem repeats. Examples are given in Table 1 below. Cyclization of some of these larger peptides is also envisioned.

Because of their relatively small size, the peptides of the invention may be directly synthesized in solution or on a solid support in accordance with conventional peptide synthesis techniques. Various automatic synthesizers are commercially available and can be used in accordance with known protocols. The synthesis of peptides in solution phase has become a well-established procedure for large-scale production of synthetic peptides and as such is a suitable alternative method for preparing the peptides of the invention. (See for example, *Solid Phase Peptide Synthesis* by John Morrow Stewart and Martin et al. *Application of Almez-mediated Amidation Reactions to Solution Phase Peptide Synthesis*, Tetrahedron Letters Vol. 39, pages 1517-1520 1998.)

Short peptide sequences, or libraries of overlapping peptides which correspond to the selected regions described herein, can be readily synthesized and then screened in assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression. Methods for production of a peptide by recombinant DNA technology are well known to those of skill in the art.

In some embodiments of the peptide of the present invention, either one or both prolines corresponding to P475 and P478 of AFP is replaced with hydroxyproline (O). Substitution of the P475 proline with serine is also permissible without loss of activity. The threonine at position T474 may be substituted with serine, valine or alanine. Valine at position V476 may be substituted with isoleucine, leucine or threonine. Examples of some of the embodiments of the invention are given in Table 1.

TABLE 1

| | |
|---|---|
| TPVN | SEQ ID NO.: 2 |
| TOVN | SEQ ID NO.: 3 |
| TPVNP | SEQ ID NO.: 4 |
| TOVNP | SEQ ID NO.: 5 |
| TPVNO | SEQ ID NO.: 6 |
| TOVNO | SEQ ID NO.: 7 |
| PVNPG | SEQ ID NO.: 8 |
| OVNOG | SEQ ID NO.: 9 |
| PVNP | SEQ ID NO.: 10 |
| KTOVN | SEQ ID NO.: 11 |
| VNOG | SEQ ID NO.: 12 |
| OVNO | SEQ ID NO.: 13 |
| SPVNP | SEQ ID NO.: 14 |
| SOVNP | SEQ ID NO.: 15 |
| SPVNO | SEQ ID NO.: 16 |
| SOVNO | SEQ ID NO.: 17 |
| VPVNP | SEQ ID NO.: 18 |
| VOVNP | SEQ ID NO.: 19 |
| VPVNO | SEQ ID NO.: 20 |
| VOVNO | SEQ ID NO.: 21 |
| APVNP | SEQ ID NO.: 22 |
| AOVNP | SEQ ID NO.: 23 |
| APVNO | SEQ ID NO.: 24 |
| AOVNO | SEQ ID NO.: 25 |
| TSVNP | SEQ ID NO.: 26 |
| TSVNO | SEQ ID NO.: 27 |
| TPVNTPVN | SEQ ID NO.: 28 |
| TPVNGGGGTPVNGGGGTPVN | SEQ ID NO.: 29 |
| TPVNOTPVNOTPVNO | SEQ ID NO.: 30 |
| TPVNOGGGGTPVNOGGGG TPVNO | SEQ ID NO.: 31 |
| TPVNOKKKTPVNOKKKTPVNO | SEQ ID NO.: 32 |
| EKTOVNOGN | SEQ ID NO.: 33 |
| TOVNOGNEK | SEQ ID NO.: 34 |
| KTOVNOG | SEQ ID NO.: 35 |
| KTOVNO | SEQ ID NO.: 36 |

TABLE 1-continued

| | |
|---|---|
| KTPVNPG | SEQ ID NO.: 38 |
| MTOVNOG | SEQ ID NO.: 39 |

Peptidomimetics

In addition to the peptide compounds described herein, the invention also contemplates that other sterically similar compounds may be formulated to mimic the key portions of the peptide structure and that such compounds may also be used in the same manner as the peptides of the invention. This may be achieved by techniques of molecular modeling and chemical design known to those of skill in the art.

In one embodiment, for example, the peptides of the invention are modified to produce peptide mimetics by replacement of one or more naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from 5 members to 4, 6, or 7 members. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics may also have amino acid residues that have been chemically modified by phosphorylation, sulfonation, biotinylation, or the addition or removal of other moieties.

A variety of techniques are available for constructing peptide mimetics with the same or similar desired biological activity as the corresponding native but with more favorable activity than the peptide with respect to solubility, stability, and/or susceptibility to hydrolysis or proteolysis (see, e.g., Morgan & Gainor, *Ann. Rep. Med. Chem.* 24, 243-252, 1989). Certain peptidomimetic compounds are based upon the amino acid sequence of the peptides of the invention. Often, peptidomimetic compounds are synthetic compounds having a three-dimensional structure (i.e. a "peptide motif") based upon the three-dimensional structure of a selected peptide. The peptide motif provides the peptidomimetic compound with the desired biological activity, i.e., binding to IAP, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life.

Peptidomimetic design strategies are readily available in the art (see, e.g., Ripka & Rich, *Curr. Op. Chem. Biol.* 2, 441-452, 1998; Hruby et al., *Curr. Op. Chem. Biol.* 1, 114-

119, 1997; Hruby & Balse, *Curr. Med. Chem.* 9, 945-970, 2000). One class of peptidomimetics comprises a backbone that is partially or completely non-peptide, but mimics the peptide backbone atom for atom and comprises side groups that likewise mimic the functionality of the side groups of the native amino acid residues. Several types of chemical bonds, e.g. ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics comprises a small non-peptide molecule that binds to another peptide or protein, but which is not necessarily a structural mimetic of the native peptide. Yet another class of peptidomimetics has arisen from combinatorial chemistry and the generation of massive chemical libraries. These generally comprise novel templates which, though structurally unrelated to the native peptide, possess necessary functional groups positioned on a nonpeptide scaffold to serve as "topographical" mimetics of the original peptide (Ripka & Rich, 1998, supra).

Pharmaceutical Compositions

The peptides of the invention are useful in a method of reducing estrogen-stimulated growth of cells by contacting the cells with the peptide. Accordingly, the compounds of the invention can be administered alone or as a pharmaceutical composition, systemically, regionally (e.g., directed towards an organ or tissue), or locally (e.g., directly into a tumor mass), in accordance with any protocol or route that achieves the desired effect. The compounds and pharmaceutical compositions can be administered as a single or multiple dose each day (e.g., at a low dose), or intermittently (e.g., every other day, once a week, etc. at a higher dose). The compounds and pharmaceutical compositions can be administered via inhalation (e.g., intra-tracheal), orally, intravenously, intraarterially, intravascularly, intrathecally, intraperitoneally, intramuscularly, subcutaneously, intracavity, transdermally (e.g., topical), transmucosally (e.g., buccal, bladder, vaginal, uterine, rectal, or nasal), by multiple administrations, sustained release (e.g., gradual perfusion over time) or a single bolus. Implantable devices, including microfabricated devices, for administering drugs are well known and are also applicable for delivering compounds of the invention to a subject.

As used herein the term "pharmaceutically acceptable" and "physiologically acceptable" includes solvents (aqueous or non-aqueous), solutions, emulsions, dispersion media, coatings, isotonic and absorption promoting or delaying agents, compatible with pharmaceutical administration. A "pharmaceutical composition" or "pharmaceutical formulation" therefore refers to a composition suitable for pharmaceutical use in a subject. The pharmaceutical compositions and formulations include a therapeutically effective amount of the compound of the invention, for example, an effective amount of a peptide or peptidomimetic, and a pharmaceutically or physiologically acceptable carrier.

As will be known to the skilled artisan, pharmaceutical compositions can be formulated to be compatible with a particular route of administration, systemic or local. Thus, pharmaceutical compositions include carriers, diluents, or excipients suitable for administration by various routes.

Formulations for enteral (oral) administration can be contained in a tablet (coated or uncoated), capsule (hard or soft), microsphere, emulsion, powder, granule, crystal, suspension, syrup or elixir. Conventional nontoxic solid carriers which include, for example, pharmaceutical grades of mannitol, lactose, starch, magnesium stearate, sodium saccharin, talcum, cellulose, glucose, sucrose, magnesium carbonate, can be used to prepare solid formulations. Supplementary active compounds (e.g., preservatives, antibacterial, antiviral and antifungal agents) can also be incorporated into the formulations. A liquid formulation can also be used for enteral administration. The carrier can be selected from various oils including petroleum, animal, vegetable or synthetic, for example, peanut oil, soybean oil, mineral oil, sesame oil. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Pharmaceutical compositions for enteral, parenteral, or transmucosal delivery include, for example, water, saline, phosphate buffered saline, Hank's solution, Ringer's solution, dextrose/saline, and glucose solutions. The formulations can contain auxiliary substances to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. Additional parenteral formulations and methods are described in Bai (1997) J. Neuroimmunol. 80:65-75; Warren (1997) J. Neurol. Sci. 152:31-38; and Tonegawa (1997) J. Exp. Med. 186:507-515. The parenteral preparation can be enclosed in ampules, disposable syringes or multiple dose vials made of glass or plastic.

Pharmaceutical compositions for intradermal or subcutaneous administration can include a sterile diluent, such as water, saline solution, fixed oils, polyethylene glycols, glycerine, propylene glycol or other synthetic solvents; antibacterial agents such as benzyl alcohol or methyl parabens; antioxidants such as ascorbic acid, glutathione or sodium bisulfite; chelating agents such as ethylenediaminetetraacetic acid; buffers such as acetates, citrates or phosphates and agents for the adjustment of tonicity such as sodium chloride or dextrose.

Pharmaceutical compositions for injection include aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, sodium chloride may be included in the composition. The resulting solutions can be packaged for use as is, or lyophilized, the lyophilized preparation can later be combined with a sterile solution prior to administration.

Pharmaceutically acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) Pharm Res. 13:1760-1764; Samanen (1996) J. Pharm. Pharmacol. 48:119-135; and U.S. Pat. No. 5,391,377, describing lipid compositions for oral delivery of therapeutic agents).

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be through nasal sprays or suppositories (see, e.g., Sayani (1996) "Systemic delivery of peptides and proteins across absorptive mucosae" Crit. Rev. Ther. Drug Carrier Syst. 13:85-184). For transdermal administration, the active compound can be formulated into ointments, salves, gels, or creams as generally known in the art. Transdermal delivery systems can also be achieved using patches.

For inhalation delivery, the pharmaceutical formulation can be administered in the form of an aerosol or mist. For aerosol administration, the formulation can be supplied in finely divided form along with a surfactant and propellant. In another embodiment, the device for delivering the formulation to respiratory tissue is in which the formulation vaporizes. Other delivery systems known in the art include dry powder aerosols, liquid delivery systems, inhalers, air jet nebulizers and propellant systems (see, e.g., Patton (1998) Biotechniques 16:141-143; Dura Pharmaceuticals, San Diego, Calif; Aradigm, Hayward, Calif.; Aerogen, Santa Clara, Calif.; and Inhale Therapeutic Systems, San Carlos, Calif.).

Biodegradable, biocompatable polymers can be used, such as ethylene vinyl acetate, polyanhydrides, polyglycolic acid, collagen, polyorthoesters, and polylactic acid. Methods for preparation of such formulations are known to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known in the art, for example, as described in U.S. Pat. Nos. 4,235,871; 4,501,728; 4,522,811; 4,837,028; 6,110,490; 6,096,716; 5,283,185; 5,279,833; Akimaru (1995) Cytokines Mol. Ther. 1:197-210; Alving (1995) Immunol. Rev. 145:5-31; and Szoka (1980) Ann. Rev. Biophys. Bioeng. 9:467). Biodegradeable microspheres or capsules or other biodegradeable polymer configurations capable of sustained delivery of small molecules including peptides are known in the art (see, e.g., Putney (1998) Nat. Biotechnol. 16:153-157). Compounds of the invention can be incorporated within micelles (see, e.g., Suntres (1994) J. Pharm. Pharmacol. 46:23-28; Woodle (1992) Pharm. Res. 9:260-265). Peptides can be attached to the surface of the lipid monolayer or bilayer. For example, peptides can be attached to hydrazide-PEG-(distearoylphosphatidyl)ethanolamine-containing liposomes (see, e.g., Zalipsky (1995) Bioconjug. Chem. 6:705-708). Alternatively, any form of lipid membrane, such as a planar lipid membrane or the cell membrane of an intact cell, e.g., a red blood cell, can be used. Liposomal and lipid-containing formulations can be delivered by any means, including, for example, intravenous, transdermal (see, e.g., Vutla (1996) J. Pharm. Sci. 85:5-8), transmucosal, or oral administration.

A pharmaceutically acceptable formulation can incorporate about 1% to 99.9% of active ingredient (e.g., peptide or peptidomimetic). The pharmaceutical compositions can be sterilized by conventional, well-known sterilization techniques, or can be sterile filtered.

Additional pharmaceutical formulations and delivery systems are known in the art and are applicable in the methods and compositions of the invention (see, e.g., Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms, Technonic Publishing Co., Inc., Lancaster, Pa., (1993); and Poznansky et al., Drug Delivery Systems, R. L. Juliano, ed., Oxford, N.Y. (1980), pp. 253-315).

The pharmaceutical formulations can be packaged in unit dosage form for ease of administration and uniformity of dosage. "Unit dosage form" as used herein refers to physically discrete unitary dosages for administration to the subject to be treated; each unit contains a predetermined quantity of compound that produces a desired effect in combination with a pharmaceutical carrier or excipient.

The invention further provides kits including invention compounds and pharmaceutical formulations thereof, optionally packaged into suitable packaging material. A kit typically includes a label or packaging insert including a description of the components or instructions for use in vitro, in vivo, or ex vivo, of the components therein. A kit can contain a collection of such components, e.g., two or more invention compounds or an invention compound in combination with a nucleic acid damaging agent or an anti-proliferative agent.

EXAMPLES

Peptide Synthesis

Peptides were synthesized using Fmoc solid-phase peptide synthesis on a Pioneer Peptide Synthesis System (PerSeptive Biosystems, Inc., Framingham, Mass.). Briefly, peptides were assembled on Fmoc-PAL-PEG-PS-resin (Applied Biosystems, Inc.) from the C-terminus, reacting the deblocked N-terminus of the incoming amino acid to form an amide bond. Amino acids used in the synthesis had their $N^{\alpha}$-amino group protected by the 9-fluorenylmethyloxycarbonyl (Fmoc) group, which was removed by piperidine at the end of each cycle in the synthesis. Side-chain protecting groups of amino acids were Asn (Trt), Gln (Trt), Glu (OtBu), Hyp (tBu), Thr (tBu) which were deprotected by trifluoroacetic acid (TFA) after peptide synthesis. The carboxyl group of the amino acid was activated with O-(7-azabenzotriazol-1-yl)-1, 1,2,3-tetramethyluronium hexafluorophosphate (HATU).

After synthesis was completed, the resin was washed three times with 100% propanol and the cleavage reaction was achieved by incubating the resin in 10 ml TFA/thioanisole/anisole/1,2-ethanedithiol (90:5:2:3) per 0.5 g resin for 5 hours. The cleavage reaction mixture was filtered using a sintered glass funnel to separate the solid resin from the peptide solution. Filtrate volume was reduced to 1 ml by evaporation facilitated with a gentle stream of air and the peptides were precipitated by addition of 15 ml dry-ice-chilled ethyl ether. The peptides were allowed to settle for 5 min at −80° C., and the supernatant was aspirated. The peptides were then washed twice in similar manner with 15 ml of ethyl acetate/diethylether (1.5:1, room temperature), the peptides were dissolved in deionized water, purified by reverse-phase HPLC, lyophilized and stored at −20° C.

The anti-estrogenic activity of each peptide was then determined using the immature mouse uterine growth assay, MCF-7 xenograft assay, and cancer prevention assay, all as previously described.

Immature Mouse Uterine Growth Assay

The anti-breast cancer activity of the linear and cyclic 8-mer and 9-mer AFP-derived peptides is well-documented using the immature mouse uterine growth assay and the human breast cancer xenograft assay; there is a strong correlation between the results of these two assays. To evaluate peptide-induced inhibition by the peptide of the present invention of estrogen-stimulated proliferation of normal tissue, the immature mouse uterine growth assay was utilized. Briefly, 13-15 day-old Swiss/Webster female mice, 6-8 g in body weight, were distributed into treatment groups of 5 mice per group so that each group contained animals of the same range of body weight. The peptide of the invention was injected i.p., s.c., or p.o. into the mice. One hour later, estradiol ($E_2$) or vehicle control for $E_2$ was injected i.p. Twenty-two hours after the second injection, uteri were harvested, trimmed free of mesenteries, and immediately weighed. The uterine weights were normalized to mouse body weights to compensate for differences in body weight among litters of the same age. Experiments employed a minimum of five mice per group and the mean normalized uterine weight±SE for each group was calculated. Percent growth inhibition in a test group was calculated from normalized uterine wet weights as described below.

$$\text{Growth inhibition (\%)} = \frac{\text{Full } E_2 \text{ stimulation} - E_2 \text{ stimulation in test group}}{\text{Full } E_2 \text{ stimulation} - \text{no } E_2 \text{ stimulation}} \times 100\%$$

Differences between groups were evaluated, employing the nonparametric Wicoxon ranks sum test. In all cases, growth inhibitions that were greater than 25% were significant at $P \leq 0.05$. Results are shown in Table 2.

TABLE 2

| Sequence | Dose ug/animal | No. of Assays | Activity % ± SD |
|---|---|---|---|
| TOVNO (SEQ ID NO.: 7) | 10 | 4 | 30 ± 7 |
|  | 1 | 6 | 33 ± 7 |
| TPVNP (SEQ ID NO.: 4) | 1 | 2 | 26 |
| TOVN (SEQ ID NO.: 3) | 1 | 2 | 29 |
| TPVN (SEQ ID NO.: 2) | 1 | 1 | 27 |
| OVNO (SEQ ID NO.: 3) | 10 | 4 | 6 ± 5 |
|  | 1 | 2 | 15 |
| PVNP (SEQ ID NO.: 10) | 1 | 1 | 10 |
| OVNOG (SEQ ID NO.: 9) | 1 | 3 | 21 ± 6 |
| KTOVN (SEQ ID NO.: 11) | 1 | 5 | 18 ± 14 |
| VNOG (SEQ ID NO.: 12) | 1 | 1 | 11 |
| Cyc-(EKTOVNOGN) (SEQ ID NO.: 33) |  | 14 | 34 ± 7 |

Xenograft Assay

The peptides of the invention were evaluated for their ability to inhibit tumor growth in a human tumor xenograft assay. Briefly, MCF-7 human breast cancer cells were obtained from ATCC® (Rockville, Md.) and were grown in DMEM supplemented with 5% FCS, 1% non-essential amino acids, 10 ng/ml insulin, 2 mM L-glutamine, 100 units/ml penicillin, and 100 μg/ml streptomycin. MCF-7 cells from culture were solidified into a fibrin clot. The tumor-containing clots were cut into pieces about 1.5 mm in diameter and implanted under the kidney capsule of severe combined immunodeficient (ICR-SCID) mice (Taconic Farms, Germantown, N.Y.) as described in Bennett et al. (Clin. Cancer Res. 1998; 4:2877-84).

Estrogen supplementation of mice was required for the growth of MCF-7 tumors. Supplementation was accomplished by s.c. implantation of a Silastic tubing capsule containing solid $E_2$ (2 mm in length) inserted on the day of tumor implantation. Tumor size was evaluated during survival laparotomy using a dissecting microscope at the time of tumor implantation and at days 15 and 30 after tumor implantation. Results are shown in FIG. 1 and are represented as the change in mean tumor volume (mm$^3$) Intraperitoneal administration of TOVNO peptide at either 10 μg/day or 1 μg/day was effective in reducing the increase in mean tumor volume. Additionally, 100 μg/day p.o. significantly decreased the increase in tumor volume.

Prevention Assay

The prevention study uses the methodology of Grubbs et al. (J. Natl. Cancer Inst. 71:625-628, 1983; Anticancer Res. 6:1395-1400, 1986) to test the ability of AFP peptides to prevent N-methyl-N-nitrosourea (MNU)-induced breast cancers in rats. Briefly, female rats were housed three per cage in a room maintained at 72±2° F. and artificially lighted for 12 hours daily. At 50 days of age, rats received a single injection of MNU (50 mg/kg body weight) or vehicle in the jugular vein. NMU was given to animals from the various treatment groups according to a predetermined randomization chart to ensure uniform distribution of the carcinogen across the groups. Beginning 10 days after MNU exposure, treatment with AFP peptide by s.c. injection occurred once daily for 23 days, a time chosen to mimic the gestation period of rats, or for loner or shorter times. The peptide was diluted in saline and was given in an investigator-blinded manner at doses between 0.03 and 0.27 mg/rat daily in a volume of 0.2 ml. The control group of animals received daily 0.2 ml s.c. injections of saline for the same time as AFP peptide administration. Animals in the positive control group received only MNU treatment and experienced the maximal number of tumors. The negative control group of rats received no MNU and no AFP peptide. These animals generated no spontaneous tumors through out the course of the study. Additional groups of animals received MNU Beginning 30 days after MNU treatment, all rats were palpated twice weekly for detection of mammary tumors, noting number, location, and size. Tumor burden was determined noninvasively with calipers by measuring the long (D) and short (d) diameters. Assuming that tumors were ellipsoid shaped, tumor volume was estimated as $(\pi/6)(d)^2(D)$. All animals were checked daily for signs of toxicity. Most studies were terminated 100 days following MNU administration and at necropsy, tumors were dissected weighed.

Figure 2:
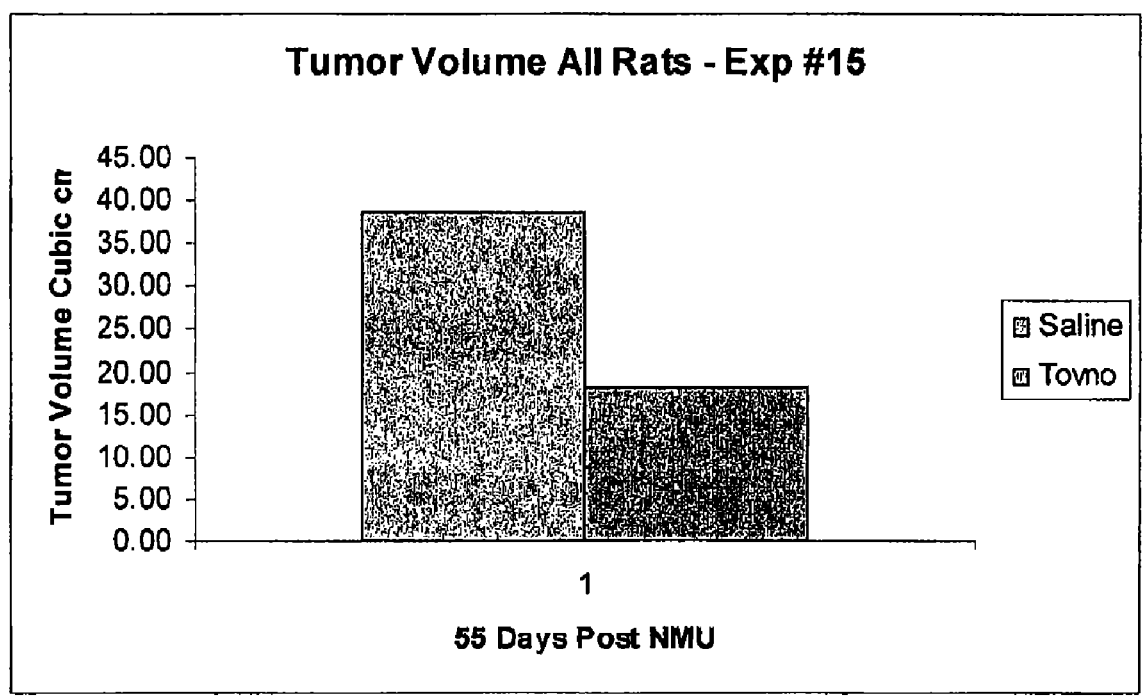
FIG. 2 is a graph showing the effect of a peptide of the invention on tumor volume in rats.

The results, as shown in FIG. 2, indicates that carcinogen (MNU)-exposed rats treated with the AFP peptide exhibited a reduction in tumor size when when compared to untreated animals with the same carcinogen exposure.

Figure 3:
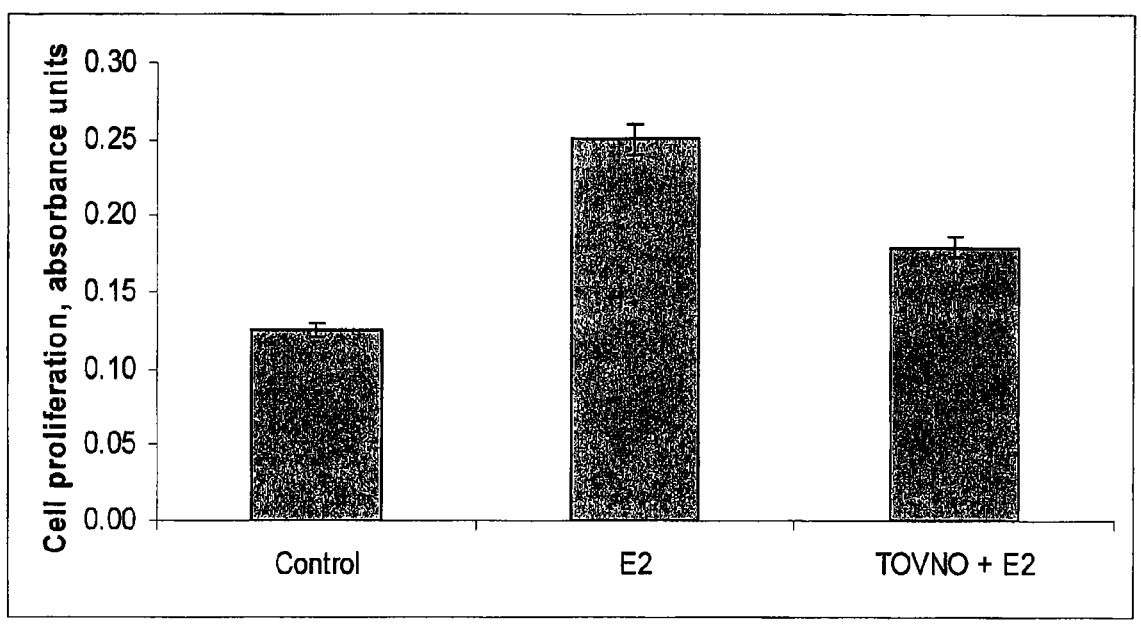
FIG. 3 is a graph showing the effect of a peptide of the invention on estrogen-stimulated T47D cell proliferation.

FIG. 3 shows the results of a study to evaluate the effect of TOVNO (SEQ ID NO.: 7) on estrogen-stimulated T47D cell proliferation. T47D cells were obtained from ATCC® (Rockville, Md.) and grown in culture according recommended protocols. Cells were treated with 1 nM estrogen or 100 nM TOVNO (SEQ ID NO.: 7)/1 nM estrogen. Control cells received 10% estrogen-free media. Cells were treated for seven days. T47D cell proliferation was reduced as compared to estrogen-stimulated cells that did not receive peptide.

Figure 4:
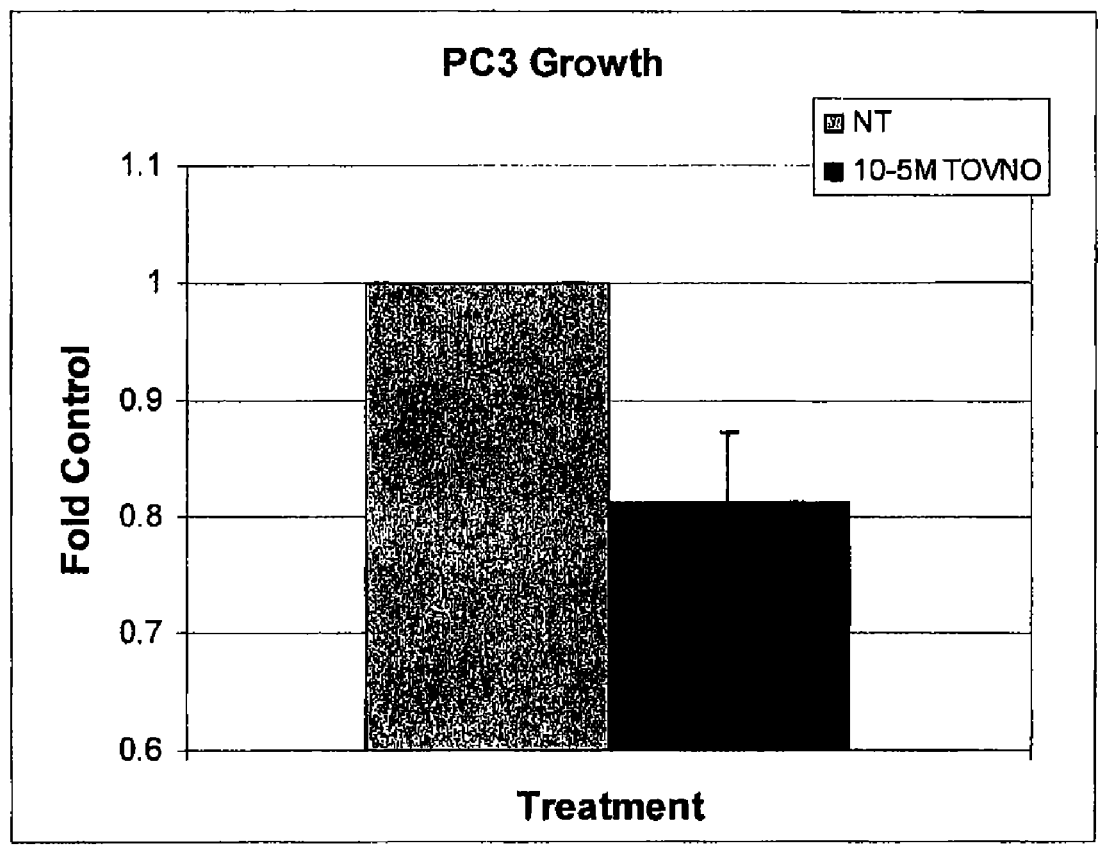
FIG. 4 is a graph showing the effects of a peptide of the invention on growth of prostate cancer cells (DC3).

The peptides of the invention were also evaluated for their ability to impact on growth of PC3 (prostate cancer cells). PC3 cells were obtained from ATCC® (Rockville, Md.) and maintained in accordance with recommended culture conditions. The results, as shown in FIG. 4, indicate that the peptides of the invention have efficacy with respect to prostate cancer as well as breast cancer.

In other experiments, peptide analogs comprising the sequences TOVN SEQ ID NO.: 3) and TPVN (SEQ ID NO.: 2) were assessed for their ability to inhibit $E_2$-stimulated growth of mouse uterus after intraperitoneal and oral administration. The results are shown in TABLE 3.

The ability to inhibit $E_2$-stimulated growth of normal mouse uterus was used as a screening assay for biological activity of AFPep analogs. In general, inhibitory activity≧20% is considered to be biologically significant. Each analog's inhibitory effect on $E_2$-stimulated growth was compared to AFPep (a positive control) and to PGVGQ (SEQ ID NO.: 44)(a negative control). PGVGQ (SEQ ID NO.: 44) (amino acids 478-482 of AFP) is a portion of the primary structure of AFP near to the anti-cancer active site of AFP and is comprised of amino acids (P, V, and G) that are important components of AFPep. A scrambled analog of AFPep was not used because some scrambled peptides retain low biological activity (data not shown). In Table 3, bold letters denote the sequences containing a putative Type I beta-turn, which was postulated to be necessary for antiestrogenic activity.

In Table 3, peptides 1-3 are AFPep and two linear 9-mer analogs. Analogs 4-11 are hydroxyproline-containing peptides of varying lengths used to assess the minimum size

TABLE 3

|     | Peptide Sequence (SEQ ID. NO.) | ↓ | Inhibition ± S.E, % |  |  |
|-----|--------------------------------|-----|---------------------|-----------------|------------------|
|     |                                |     | Immature mouse uterine growth | | T47D cell |
|     |                                |     | Intraperitoneal | Oral Gavage | proliferation |
| 1.  | cyclo[EKTOVNOGN]           | 33  | 33 ± 7*    | 35 ± 4*  | 51 ± 4* |
| 2.  | EKTOVNOGN                  | 33  | 30 ± 2*    | 32 ± 3*  | 41 ± 9* |
| 3.  | TOVNOGNEK                  | 34  | 32 ± 2*    | 36 ± 6*  | 40 ± 7* |
| 4.  | KTOVNOG                    | 35  | 35 ± 6*    |          | 41 ± 4* |
| 5.  | KTOVNO                     | 36  | 32 ± 5*    |          | 43 ± 4* |
| 6.  | KTOVN                      | 11  | 30 ± 4*    |          | 33 ± 9* |
| 7.  | TOVN                       | 3   | 21 ± 4*    |          | 18 ± 2* |
| 8.  | TOVNO                      | 7   | 38 ± 2*    | 30 ± 5*  | 48 ± 5* |
| 9.  | OVNO                           | 13  | 7 ± 3      | 12 ± 2   | 8 ± 3   |
| 10. | OVNOG                          | 9   | 25 ± 4*    |          | 24 ± 1* |
| 11. | VNOG                           | 12  | 5 ± 3      |          | 16 ± 6  |
| 12. | MTPVNPG                    | 37  | 18 ± 1     |          |         |
| 13. | KTPVNPG                    | 38  | 34 ± 2*    |          |         |
| 14. | MTOVNOG                    | 39  | 28 ± 2*    |          |         |
| 15. | EMTOV                          | 40  | 1 ± 1      |          |         |
| 16. | EKTOV                          | 41  | 9 ± 1      |          | 8 ± 2   |
| 17. | EKTPV                          | 42  | 0          |          |         |
| 18. | EMTPV                          | 43  | 5 ± 4      |          |         |
| 19. | TPVN                       | 2   | 29 ± 1*    |          |         |
| 20. | TPVNP                      | 4   | 27 ± 1*    |          |         |
| 21. | PVNP                           | 10  | 6 ± 3      |          |         |
| 22. | PGVGQ                          | 44  | 0          |          | 3 ± 1   |

Bold letters represent the residues that form the putative Type I beta-turn (8, 9). All peptides were administered at a dose of 1 μg/mouse intraperitoneally or 10 μg/mouse by oral gavage. In culture, T47D cells were treated with each peptide at a concentration of 1 μM.
*p < 0.05 as compared to the group stimulated with $E_2$ alone. Wilcoxon Rank-Sum Test.

required to maintain inhibitory activity. Analogs 12-14 are 7-mers that lack the N-terminal amino acid (E) of AFPep. Analogs 15-18 are 5-mers from the N-terminus of EKTOVNOGN (analog 2, SEQ ID NO).: 33), but outside the putative pharmacophoric region. Analogs 17-21 are the proline-containing peptides. Much of the Replica Exchange Molecular Dynamics (REMD) work had modeled proline instead of hydroxyproline; hydroxyproline had been introduced to increase hydrophilicity.

Mesfin et al. showed that the minimum size required to maintain antiestrogenic activity was 8 amino acids and that a 7-mer peptide, MTPVNPG (analog 12, SEQ ID NO.: 37), had substantially reduced antiestrogenic properties. Kirschner et al. suggested that TOVN (analog 7, SEQ ID NO.: 3) would retain antiestrogenic activity. In Table 3, analogs 4-11 were used to determine the minimum size required to maintain antiestrogenic activity. In contrast to results reported by Mesfin et al, linear analogs of AFPep that were less than 8 amino acids maintained antiestrogenic activity. Even TOVN (SEQ ID NO.:3) had weak antiestrogenic activity. However, OVNO (SEQ ID NO.: 13) lacked antiestrogenic activity. The most effective analog was 5-mer TOVNO (analog 8. SEQ ID NO.: 7), which significantly inhibited $E_2$-stimulated uterine growth.

It was suggested that AFPep analogs forming putative Type I beta-turns within TPVN (SEQ ID NO.: 2)/TOVN (SEQ ID NO.: 3) sequence should retain antiestrogenic activity. Table 3 shows that all analogs containing a putative Type I beta-turn (signified by bold-face font) significantly inhibited estrogen-stimulated growth of immature mouse uterus except for MTPVNPG (analog 12, SEQ ID NO.: 37). Analogs not exhibiting a putative Type I beta-turn had little or no antiestrogenic effect except for OVNOG (analog 10, SEQ ID NO.: 9), which weakly inhibited $E_2$-stimulated uterine growth.

Proline-containing peptides (analogs 17-21) replicated the activity of hydroxyproline-containing peptides (analogs 4-11), which showed that there is not significant difference in biological activity when proline is replaced by hydroxyproline.

Noting that if AFPep (cyclo[EKTOVNOGN] SEQ ID NO.: 33) were to be cleaved by a trypsin-like protease in vivo, the product would be TOVNOGNEK (analog 3. SEQ ID NO.: 34), we assessed the effectiveness of this analog as an antiestrogen. TOVNOGNEK SEQ ID NO.: 34) significantly inhibited $E_2$-stimulated uterine growth and there was no significant difference between its inhibitory activity and that of AFPep. Analog 2 (EKTOVNOGN SEQ ID NO.: 33) was also active at this dose, which confirmed work done in previous studies.

REMD had suggested that MTPVNPG (SEQ ID NO.: 37, analog 12 of Table 3) contains a putative Type I beta-turn and should significantly inhibit $E_2$-stimulated uterine growth. Earlier studies found that MTPVNPG (SEQ ID NO.: 37) was difficult to synthesize by Fmoc solid-phase peptide chemistry and had little antiestrogenic activity. In part this may have led to an earlier conclusion that EMTPVNPG (SEQ ID NO.: 1) was the minimum size AFP-derived peptide able to retain antiestrogenic activity. We also found this analog difficult to synthesize by Fmoc chemistry. Therefore, Boc-solid-phase peptide chemistry was used to synthesize MTPVNPG (SEQ ID NO.: 37) and three related linear 7-mer peptides (KTOVNOG (SEQ ID NO.: 35), KTPVNPG (SEQ ID NO.: 38), and MTOVNOG (SEQ ID NO.: 39); analogs 4, 13, and 14 of Table 3). The purity and activity of each peptide were the same after both methods of peptide synthesis; KTOVNOG (SEQ ID NO.: 37), KTPVNPG (SEQ ID NO.: 38), and MTOVNOG (SEQ ID NO.: 39) significantly inhibited $E_2$-stimulated uterine growth, whereas MTPVNPG(SEQ ID NO.: 37) showed significantly less activity.

The antiestrogenic properties of peptides outside the pharmacophoric region (EMTOV (SEQ ID NO.: 40), EKTOV (SEQ ID NO.: 41), EKTPV (SEQ ID NO.: 42), and EMTPV (SEQ ID NO.: 43) (analogs 15-18) were also evaluated and found to have little or no antiestrogenic activity (Table 3.)

The activities of three active peptides (EKTOVNOGN (SEQ ID NO.: 33), TOVNOGNEK (SEQ ID NO.: 34), and TOVNO (SEQ ID NO.: 7)), and one inactive peptide (OVNO SEQ ID NO.: 13) were further compared to AFPep for their ability to inhibit $E_2$-stimulated growth of mouse uterus after oral administration. As shown in Table 3, analogs active by the parenteral route were also active by the oral route of administration, and their activities were comparable to those of AFPep.

A number of AFPep analogs were assessed for in vitro anticancer activity. Analogs containing the putative pharmacophore directly interfered with the growth stimulatory effects of estrogen on T47D human breast cancer cells in culture (Table 3), but they did not affect the basal growth of these cells (data not shown). TOVN (SEQ ID NO.: 3) had very weak inhibitory activity against $E_2$-stimulated T47D cell growth. OVNO (SEQ ID NO.: 13) lacked inhibitory activity. TOVNO (SEQ ID NO.: 7) significantly inhibited $E_2$-stimulated T47D human breast cancer cell growth and was comparable to AFPep in this activity (Table 3). TOVNOGNEK (SEQ ID NO.: 34) was also comparable to AFPep in its ability to inhibit the $E_2$-stimulated growth of T47D human breast cancer cells.

Figure 5:
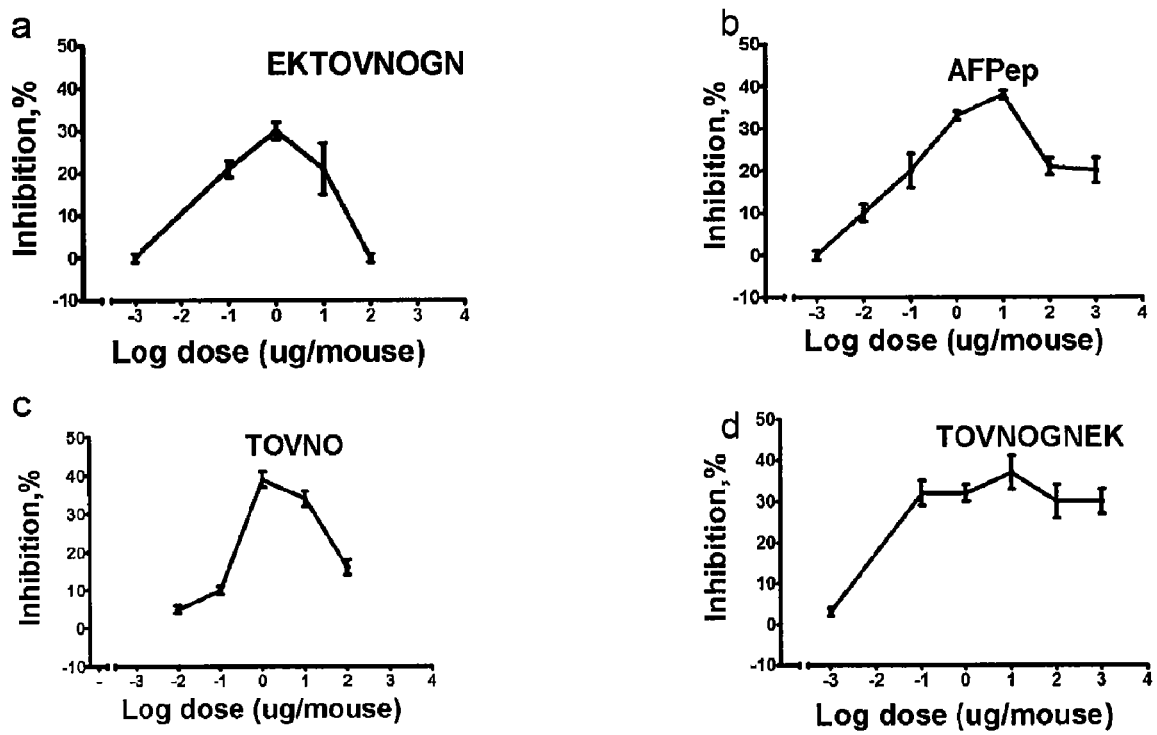
FIGS. 5a-d are graphs showing the dose-response profile of AFPep analogs with respect to inhibition of $E_2$-stimulated uterine growth.

As shown in FIG. 5a, the linear 9-mer precursor (analog 2) of AFPep exhibited a biphasic dose-response curve in the $E_2$-stimulated uterine growth assay. Cyclization (to yield AFPep) attenuated but did not completely eliminate this loss of activity with increasing doses (FIG. 5b). The AFPep dose-response profile was compared to the profiles seen from two of the more active linear peptides, TOVNO (SEQ ID NO.: 7) and TOVNOGNEK (SEQ ID NO.: 34). FIG. 5c shows a biphasic dose-response curve for linear TOVNO (SEQ ID NO.: 7). TOVNO (SEQ ID NO.: 7) inhibited $E_2$-stimulated uterine growth in a dose-dependent manner up to 1 μg/mouse, but thereafter it lost inhibitory effect with increasing dose. FIG. 5d shows that TOVNOGNEK (SEQ ID NO.: 34) inhibited $E_2$-stimulated uterine growth and maintained its inhibitory effect at high doses.

Figure 6:
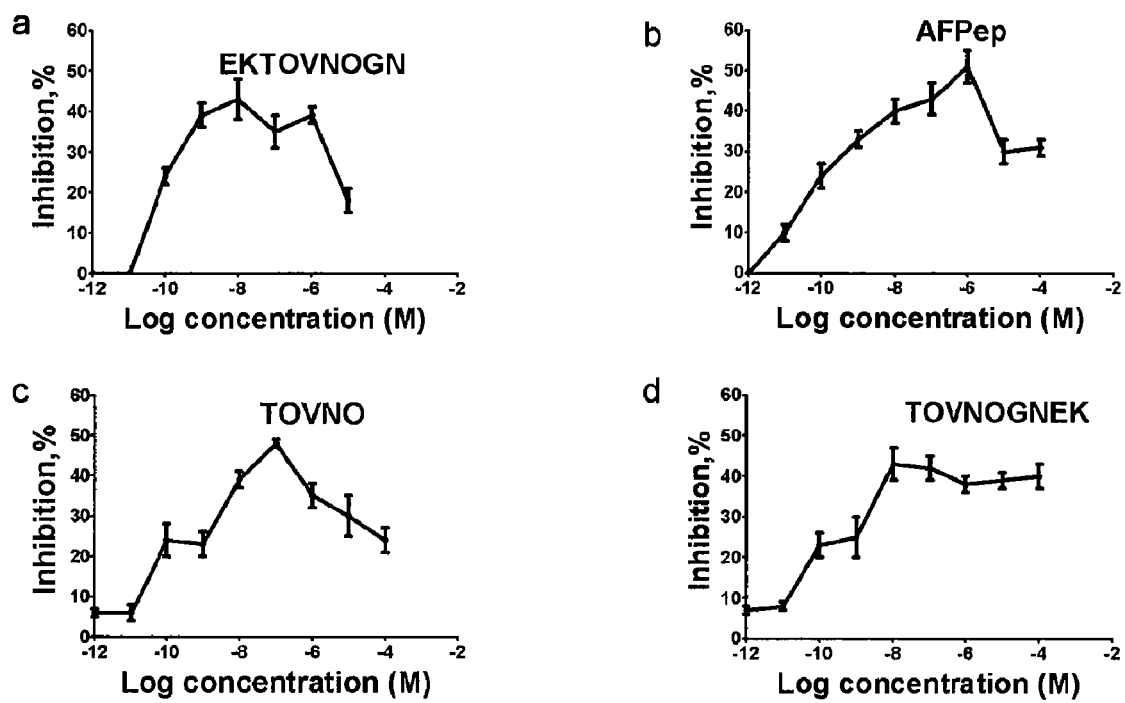
FIGS. 6a-d are graphs showing the dose-response profile of AFPep analogs with respect to inhibition of T47D human breast cancer cell proliferation

FIG. 6 shows the dose response profiles of these four active peptides against $E_2$-stimulated growth of human breast cancer cells in vitro. EKTOVNOGN (SFQ ID NO.: 33) inhibited $E_2$-stimulated T47D cell growth at low concentrations but lost activity at high concentrations, leading to a biphasic dose response curve (FIG. 6a). AFPep inhibited the $E_2$-stimulated growth of T47D cells in a concentration dependent manner up to $10^{-6}$M but lost activity at higher concentrations (FIG. 6b). The shorter 5-mer peptide, TOVNO (SEQ ID NO.: 7), was an effective inhibitor of $E_2$-stimulated growth of T47D human breast cancer cells in a concentration-dependent manner up to $10^{-7}$M, but lost activity with increasing concentration thereafter (FIG. 6c). However, TOVNOGNEK (SEQ ID NO.: 34) inhibited $E_2$-stimulated T47D cell growth in a concentration dependent manner and maintained its activity with increasing concentrations (FIG. 6d) at concentrations as high as $10^{-4}$ M.

Figure 7:
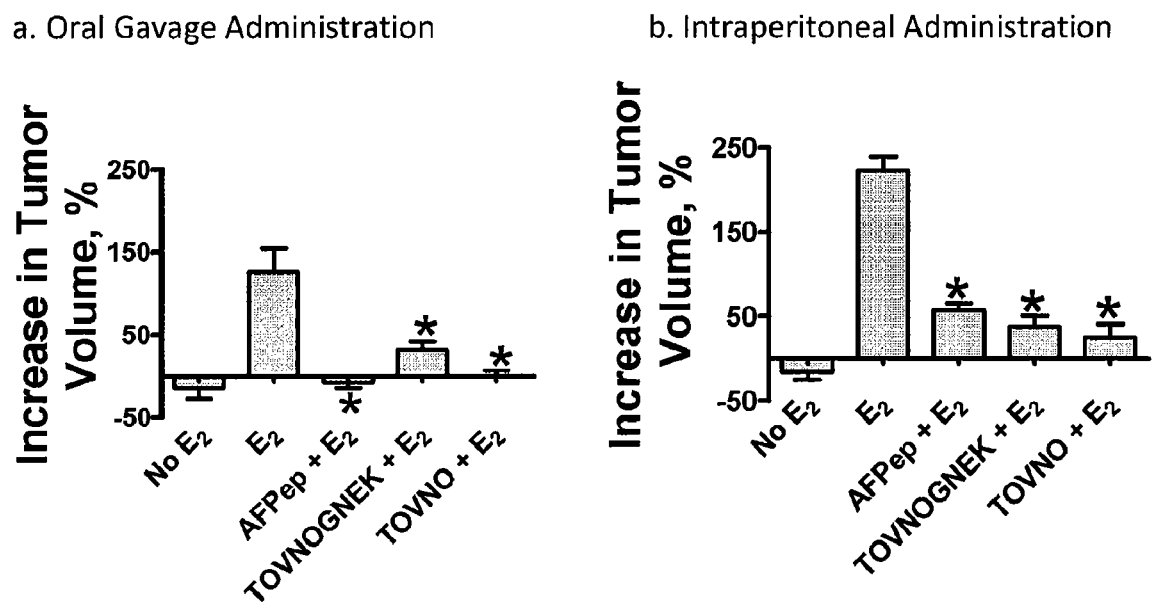
FIGS. 7a-b are graphs showing the ability of peptide analogs of AFPep to block the growth of human tumor xenografts in SCID mice.

The T47D human breast cancer cell line is responsive in culture, but it was a less reliable tool when grown as a xenograft tumor in immune deficient mice, having a take-rate of <60% in these mice. However, the MCF-7 human breast cancer cell line has a tumor take-rate of 100% in immune deficient mice and is completely dependent on $E_2$ for growth in these mice (2). Consequently, MCF-7 xenografts were used as a model for ER+human breast cancer to evaluate, in vivo, the effectiveness of TOVNO (SEQ ID NO.: 7) and TOVNOG-NEK (SEQ ID NO.: 34) as anticancer agents. As shown in FIG. 7, MCF-7 human breast cancer tumors were dependent on supplemental estrogen for growth as a xenograft in male SCID mice. AFPep, TOVNOGNEK (SEQ ID NO.: 34), or TOVNO (SEQ ID NO.: 7), each given once a day at a dose of 100 µg by oral gavage (FIG. 7a) or 10 µg per mouse i.p., (FIG. 7b) significantly inhibited the growth of ER+human MCF-7 breast cancer tumors.

LITERATURE CITED

1. G. I. Abelev, *Advances in Cancer Research* 14, 295 (1971).
2. H. I. Jacobson, J. A. Bennett, G. J. Mizejewski, *Cancer Research* 50, 415 (Jan. 15, 1990).
3. J. A. Bennett, S. J. Zhu, A. Pagano-Mirarchi, T. A. Kellom, H. I. Jacobson, *Clinical Cancer Research* 4, 2877 (November, 1998).
4. F. B. Mesfin, T. T. Andersen, H. I. Jacobson, S. Zhu, J. A. Bennett, *Journal of Peptide Research* 58, 246 (September 2001).
5. L. A. DeFreest et al., *Journal of Peptide Research* 63, 409 (May, 2004).
6. F. B. Mesfin, J. A. Bennett, H. I. Jacobson, S. J. Zhu, T. T. Andersen, *Biochimica Et Biophysica Acta-Molecular Basis of Disease* 1501, 33 (Apr. 15, 2000).
7. J. A. Bennett, F. B. Mesfin, T. T. Andersen, J. F. Gierthy, H. I. Jacobson, *Proc Natl Acad Science* 99, 221T1 (February 2002).
8. L. E. Eisele, F. B. Mesfin, J. A. Bennett, T. T. Andersen, H. I. Jacobson, D. D. Vakharia, R. MacColl, G. J. Mizejewski, *Journal of Peptide Research* 57, 539 (June 2001).
9. L. E. Eisele, F. B. Mesfin, J. A. Bennett, T. T. Andersen, H. I. Jacobson, H. Soldwedel, R. MacColl, G. J. Mizejewski, *Journal of Peptide Research* 57, 29 (January 2001).
10. S. Aggarwal, P. Singh, O. Topaloglu, J. T. Isaacs, S. R. Denmeade, *Cancer Research* 66, 9171 (Sep. 15, 2006).
11. S. Aggarwal, J. L. Harden, S. R. Denmeade, *Bioconjugate Chem.*, 17, 335 (Feb. 8, 2006).
12. P. D. O'Leary, R. A. Hughes, *The Journal of Biological Chemistry*, 278, 25738 (Jul. 11, 2003).

What is claimed is:

1. A synthetic linear peptide comprising the amino acid sequence TOVNOGNEK (SEQ ID NO.: 34).

2. The synthetic linear peptide of claim 1, wherein said peptide has anti-estrotrophic activity.

3. A synthetic peptide comprising one or more tandem repeats of SEQ ID NO.: 34.

4. The synthetic peptide of claim 3, wherein said tandem repeats are separated by at least one spacer amino acid.

5. A pharmaceutical composition comprising the peptide of claim 1 and a pharmaceutically acceptable carrier.

6. A method of reducing estrogen-stimulated growth of cells, the method comprising exposing said cells to the peptide of claim 1.

7. The method of claim 6, comprising exposing the cells to tamoxifen before, during, or after exposing the cells to the peptide.

8. A method for the treatment of breast cancer in a patient comprising administering to the patient a therapeutically effective amount of the peptide of claim 1.

* * * * *